United States Patent [19]
Diamondis

[11] Patent Number: 5,489,780
[45] Date of Patent: Feb. 6, 1996

[54] RADON GAS MEASUREMENT APPARATUS HAVING ALPHA PARTICLE-DETECTING PHOTOVOLTAIC PHOTODIODE SURROUNDED BY POROUS PRESSED METAL DAUGHTER FILTER ELECTRICALLY CHARGED AS PO-218 ION ACCELERATOR

[76] Inventor: Peter J. Diamondis, 1155 Redwood Rd., Merritt Island, Fla. 32952

[21] Appl. No.: 333,529

[22] Filed: Nov. 2, 1994

[51] Int. Cl.$^6$ .............................. G01J 5/10; G01V 5/00; G01N 23/10; H01J 47/18

[52] U.S. Cl. .................... 250/370.02; 250/253; 250/374; 250/435

[58] Field of Search .............................. 250/370.02, 253, 250/261, 374, 380, 472.1, 435, DIG. 2

[56] References Cited

U.S. PATENT DOCUMENTS 4,871,914  10/1989  Simon et al. .......................... 250/370

OTHER PUBLICATIONS

"Design of a Continuous Digital-Output Environmental Radon Monitor"; McDonald E. Wrenn et al.; *IEEE Transactions on Nuclear Science*, vol. NS–22, Feb., 1975, pp. 645–647.

"Use of Electrostatic Collection of $^{218}$Po for Measuring Rn"; Philip K. Hopke; *Health Physics*, vol. 57, No. 1 (Jul.), pp. 32–42; 1989.

"Continuous Registration of $^{222}$Rn Concentration in Air Varying with Time"; E. Albrecht et al.; Vienna: International Atomic Energy Agency, 1967, pp. 643–650.

"A Passive Environmental Radon Monitor"; Andreas C. George; Health and Safety Laboratory; pp. 25–30.

"Development of a Rapid Response Radon Monitor" prepared for: United States Department of the Interior Bureau of Mines pp. 1–66.

"Influence of Electric Charge and Humidity Upon the Diffusion Coefficient of Radon Decay Products"; Porstendorfer et al.; *Health Physics* vol. 37 (Aug.); pp. 191–199.

"Method for the Determination of $^{222}$Rn (Radon)—and $^{220}$Rn (Thoron)—Exhalation Rates Using Alpha–Spectroscopy"; Keller et al.; *Radiation Protection Dosimetry*, vol. 3 No. 1/2, Nuclear Technology Publishing, 1982; pp. 83–89.

"The Measurement of Low Concentrations of Radon in Air"; Washington et al., Atomic Energy Control Board; pp. 559–561.

"Radon Measurement Activities and Instruments Designed at Studsvik Energiteknik AB", *Radiation Protection Dosimetry*, vol. 7, No. 1–4, pp. 215–218, Nuclear Technology Publishing; pp. 215–218.

"Radon–222 in the Antarctic Peninsula During 1986"; Pereira et al.; Instituto de Pesquisas Espaciais; pp. 1–13.

"Direct Measurement of Radon Exhalation From Surfaces"; Ackers; *Radiation Protection Dosimetry*; vol. 7 No. 1–4; Nuclear Technology Publishing; pp. 199–201.

"A $^{222}$Rn Monitor Using a Spectroscopy"; *Health Physics*, vol. 50, No. 5 (May), pp. 645–646, 1986.

*Primary Examiner*—Constantine Hannaher
*Assistant Examiner*—Virgil O. Tyler
*Attorney, Agent, or Firm*—Charles E. Wands

[57] ABSTRACT

A radon detector employs an electrically charged pressed, porous metal filter that allows radon gas diffusion, while blocking ambient light, so that it readily traps both attached and unattached Po-214 and Po-218 ions, that may be present in gas passing through the filter, the filter being charged positively relative to an unbiased PN junction of a photodiode detector within a detection chamber. As a consequence, radon daughter products are prevented from corrupting the radon measurement. Since no voltage differential is applied across its PN junction, the photodiode detector operates in a photovoltaic mode, which avoids the problem of Schottky noise, producing low amplitude current pulses, which are amplified, passband filtered, and thresholded to provide well-defined pulses that are counted over a given measurement interval and converted to radon concentration in terms of picocuries per liter.

27 Claims, 2 Drawing Sheets

RADON GAS MEASUREMENT APPARATUS HAVING ALPHA PARTICLE-DETECTING PHOTOVOLTAIC PHOTODIODE SURROUNDED BY POROUS PRESSED METAL DAUGHTER FILTER ELECTRICALLY CHARGED AS PO-218 ION ACCELERATOR

FIELD OF THE INVENTION

The present invention relates to radon gas measurement devices, and is particularly directed to a radon gas detector that employs a photovoltaic alpha particle detecting photodiode disposed within a radon gas detection chamber, surrounded by a light and radon daughter product-blocking, blocking, but radon gas porous, pressed metal filter, which is electrically charged to create an electric field that accelerates Po-218 ions onto the collection surface of the photodiode.

BACKGROUND OF THE INVENTION

Radon is an invisible, odorless and chemically inactive radioactive gas that is produced by the decay of uranium ore, such as radium, actinium, or thorium. As described in the introductory (background) portion of my U.S. Pat. No. 5,319,208, issued Jun. 7, 1994, entitled "Forced Air Flow Radon Detector Having Electrically Conductive Inlet and Exhaust Filters," during its decay process, radon produces several high energy alpha particles and solid, radioactive decay products, termed daughter products. In particular, Rn222 decays by emitting an alpha particle having an energy of 5.5 MeV (million electron volts) to produce a radioactive daughter ion Po218. Po218 then decays by emitting an alpha particle having an energy of 6.0 MeV to produce a radioactive daughter ion Po214. The Po214 ion subsequently decays by emitting an alpha particle having an energy of 7.7 MeV to produce radioactive daughter Po210. Po210, which has a half life of 20 years, eventually decays by emitting an alpha particle having an energy of 5.3 MeV.

Because inhaling radon and its radioactive decay products causes irradiation of lung tissue, prolonged exposure to high concentrations of radon significantly increases the risk of developing cancer. It has been reported that the U.S. Environmental Protection Agency estimates exposure to naturally occurring radon leads to 21,000 lung cancer deaths nationwide each year, making radon the nation's primary environmental health threat and second only to cigarette smoking as a cause of fatal lung cancer.

Although it was originally believed that dangerous levels of radon occurred primarily in uranium mines or laboratories having large quantities of uranium, various studies have indicated that radon produced by the decay of radioactive ore in the rock and soil migrates to the earth's surface and becomes trapped in residential buildings, where indoor concentrations of radon eventually build up to dangerous levels, thereby creating a significant residential health hazard. Indeed, indoor radon is now believed to be a greater radiological hazard to the general population than all other natural and man-made radiation sources combined. It has been estimated that between 6 and 9 million homes in the United States have radon levels above 4 pCi/l (pico Curies per liter of air), the level above which the Environmental Protection Agency urges remedial action.

Whether the occupants of a building are at risk due to unacceptably high concentrations of radon can be determined only by actual measurement of air samples within the building. The tremendous volume of testing required to identify those buildings which are at risk has created a need for a radon gas detector which possesses the following characteristics. First the measurement must be reasonably fast. The instrument must also perform a high precision measurement. It should also be relatively low cost, in order to be practically affordable, and it should not require a skilled operator or the need for follow on laboratory analysis. In addition, the instrument should be capable of measuring radon concentration in pCi/l or radon daughter product concentration in working level (WL) units, or both.

Various types of equipment and components have been proposed to date for radon detection. For example, an article by M. Wrenn et al, entitled: "Design of a Continuous Digital-Output Environmental Radon Monitor," Institute of Electrical and Electronics Engineers Trans. Nucl. Sci. NS-22:645–648, 1975, and an article by P. Hopke et al, entitled: "Use of Electrostatic Collection of Po-218 for Measuring," Rn. Health Physics, Vol. 57, No. 1 (July), pp. 39–42, 1989; describe the use of an electrostatic field for Po-218 collection. In particular, Wrenn et al describe placing a polyurethane foam radon daughter filter over a detector with a coarse metal screen over it, to form a positive (anode) electrode. A piece of aluminized mylar with phosphors on the surface is used as the negative electrode (cathode). Underneath the mylar is a photomultiplier tube that detects scintillations produced on the phosphor by alpha particles from the decay of deposited Po-218 ions.

An article by E. Albrecht et al, entitled: "Continuous Registration of Rn-222 Concentration in Air Varying with Time," in Assessment of Airborne Radioactivity in Nuclear Operations. Vienna, International Atomic Energy Agency, 1967 describes a device in which radon and its daughters were pumped into a separation chamber through a membrane to filter out the existing daughters. A surface barrier silicon photodiode was the detector with a gold metal barrier on the surface as the cathode of the electric field. The conductive inner surface of the separation chamber served as the anode. The photodiode was biased with 35 volts.

An article by A. C. George, entitled: "A Passive Environmental Radon Monitor," in Radon Workshop, February, 1977, New York: Health and Safety Laboratory; HASL-325, pp 25–30, 1977, describes the use of an electric filed to accumulate Po-218 ions onto a LiF crystal detector. This is a passive detector that stores beta and gamma radiation that can later be read out on a thermoluminescent dosimeter (TLD) analyzer. The radon daughter filter used was a paper filter. The anode device was an inverted metal funnel with a perforated metal disk at the large opening. The cathode was a bolt with the TLD cemented to it. This radon monitor is not a real time measuring device, since processing of the TLD is required after the measurement to determine radon concentration.

For descriptions of other proposals for radon detection, attention may be directed to an article by R. Miller, entitled: "Development of a Rapid Response Radon Monitor," Final report to Bureau of Mines, Denver, Colo., U.S. Bureau of Mines, Contract No. HO262019, 1979; an article by J. Porstendorfer et al, entitled: "Influence of Electric Charge and Humidity Upon the Diffusion Coefficient of Radon Decay Products," Health Phys. 15, pp191–199, 1979; an article by G. Keller et al entitled: "Method for the determination of Rn-222 (Radon) and Rn-230 (Thoron) Exhalation Rates Using Alpha Spectroscopy," Radiat. Prot. Dosim.

3(½), pp 83–89, 1982; an article by R. Washington et al, entitled: "The Measurement of Low Concentrations of Radon in Air," Health Phys 45, pp 559–561, 1983; an article by H. Tovedal, entitled: "Radon Measurement Activities and Instruments Designed at Studsvik Energiteknik," A. B. Radat Prot Dosim. 7(1–4), pp 215–218, 1984, an article by E. Pereira et al, entitled: "Radon-222 in the Antarctic Peninsula during 1986," Radiat. Prot. Dosim., 1989; an article by J. Ackers, entitled: "Direct Measurement of Radon Exhalation from Surfaces," Radiat. Prot. Dosim. 7(1–4), pp 199–201, 1984; and an article by S. Watnick et al, entitled: "Rn-222 Monitor Using a Spectroscopy," Health Phys. 50, pp 645–646, 1986.

Currently available radon detectors include scintillation and photomultiplier detectors, solid state junction and surface barrier photodiode detectors, gas proportional detectors, alpha track detectors, and charcoal canisters. However, none of these radon detectors has all of the features currently desired in a radon detector.

For example, Honeywell Inc. has marketed a device that uses a relatively simple and compact open photodiode detector to sense alpha particle emission. However, because its radon daughter filter porosity is only 0.8 microns, its response time is inordinately long. Another consideration in the design of a radon detector is the presence of electrical noise (always a problem in any electronic instrumentation).

In a radon measurement device, noise can be considered to be any undesirable electrical signal or pulse that can be interpreted as the desired pulse, thereby producing an error in the measurement. False pulses produced by electrical noise inflate the measurement of radon or produce a "background" pulse count, even in the absence of radon.

One attempt to solve the noise problem is described in the U.S. Patent to W. Simon et al, U.S. Pat. No. 4,871,914, entitled: "Low-Cost Radon Detector." The patented device describes the use of a dummy circuit with active elements (amplifier) parallel to the detector circuit, in order to cancel out transient noise and some microphonics. Photodiode detectors having special bonding of the leads without lead solder are employed avoid possible alpha emitting contaminants in lead. These measures require custom fabrication of the photodiode assemblies and many additional components including amplifiers, all adding to the cost of the instrument but not contributing to the reduction of all the noise components.

Advantageously, the device described in my above-referenced patent is able to provide the previously described characteristics that are desired of a radon device, without the drawbacks of other currently commercially available devices. For this purpose, my patented radon gas detector is comprised of a housing having an air inlet port leading to an interior, a radiation detection (e.g. alpha particle measurement) chamber and an air exhaust port leading from the interior chamber to the exterior of the housing. The interior chamber is closed to the entry of ambient light by means of a pair of light-obstructing baffle structures that respectively couple the air inlet and air exhaust ports to the interior chamber. The light obstructing baffle structure between the air inlet port and the interior chamber has an air passageway whose length is in excess of its widthwise dimension, so as to effectively prevent the entry of ambient light into the interior chamber by way of the air inlet port.

Coupled with the air inlet port is a first removable, electrically conductive mesh filter, through which air entering the air inlet port passes in the course of its movement to the interior chamber. Similarly, coupled with the air exhaust port is a second electrically conductive mesh filter. A significant feature of my patented device is fact that each electrically conductive mesh filter traps (ionic) Po-218 and Po-214 radon daughter products before they can enter into the interior chamber, while simultaneously allowing substantial air flow (through the openings in the mesh).

When air is drawn into the alpha particle measurement chamber under the control of a forced air movement device, such as an exhaust fan disposed in the air flow path through the exhaust port from the interior chamber, a substantial quantity of air per unit time can be actively circulated through the measurement chamber, thereby significantly reducing the length of time required to obtain a meaningful measurement of radon concentration within the ambient air under test. Disposed within the measurement chamber is a radiation (e.g. alpha particle responsive) detector in the form of an open photodiode array, which is exposed to incident alpha particle emissions from the radon gas as it is drawn through the interior chamber by the operation of the exhaust fan.

SUMMARY OF THE INVENTION

Now although my patented radon detector provides a significant improvement over conventional types of devices, I have found that the daughter product-filtering action of its electrically conductive filters and forced air flow system can be effectively achieved by replacing the mesh-configured intake filter with a pressed, porous metal filter, and charged positively relative to the photodiode to create an electrostatic field that accelerates and focuses Po-218 ions, into which radon gas that has entered the measurement chamber decays, onto the collection surface of an alpha particle detecting photodiode element. Because of the porosity and light blocking capabilities of the pressed metal filter, the need for a separate forced air flow control device (exhaust fan) and second conductive mesh filter at an exhaust port becomes unnecessary, thereby reducing the hardware complexity and cost of the device.

In accordance with a preferred embodiment of the radon gas detector of the present invention, the porous, pressed metal filter forms an electrically conductive contaminant and light-filtering enclosure that is joined at its base in sealed engagement with a circuit board upon which electrical signal processing components of the detector are mounted. The physical composition of the porous, pressed metal filter provides a generally random diffusion path that allows radon-containing gas to pass through it, yet prevents the entry of light and radon daughter products into an interior portion of the filter enclosure.

The geometry and porosity of the pressed metal filter causes both attached and unattached Po-214 and Po-218 ions to be captured prior to their entering detection chamber, so that radon daughter products are prevented from corrupting the radon measurement process carried out within the detection chamber. The diffusion path through the porous metal filter is tortuous to light, so that it very effectively blocks the entry of light and other electromagnetic radiation into the interior of the detector, whereby an alpha particle-detecting photodiode is not affected by ambient lighting conditions of the environment in which the radon detector is placed. The pressed metal filter enclosure around the photodiode element shields it from electromagnetic interference (EMI). No voltage differential is applied across the anode and cathode electrodes of the photodiode, so that its photosensitive PN junction is unbiased. As a result, the photodiode element operates in a photovoltaic mode, which avoids the problem of Schottky noise. The photodiode produces low amplitude current pulses in response to the impingement of alpha particles.

Because of the physical properties of the porous metal filter, alpha particles incident upon the photodiode element, which are manifested as current pulses, are effectively only those which result from the decay of radon-containing gas that has entered the detection chamber. To optimize the ability of the photodiode to detect alpha particle emissions, a high voltage is applied to the filter enclosure, so as to establish a static electric field between the electrically conductive filter enclosure and the photodiode element. This high voltage creates an electric field that causes Po-218 ions to be rapidly repelled away from the filter enclosure and accelerated and focussed onto photodiode element, so that they may quickly deposit upon the collection surface of the photodiode, where they decay, producing detectable alpha particles.

To reduce potential electromagnetic interference (EMI) coupling into the signal leads of the high voltage source, an AC bypass capacitor is connected between the positive high voltage terminal and a housing or instrument ground. The applied electric field also serves to minimize the opportunity of trace amounts of water molecules or other components, such as $O_2$, NO, $NO_2$, and $NH_3$, that may be present in air diffused into interior chamber, to neutralize Po-218 ions and hinder their deposition on the photodiode's collection surface. This elimination of the variability of alpha particle detection measurements due to changes in humidity enhances the accuracy of the detector. Since the accelerating electric field increases the number of Po-218 ions depositing upon the collection surface of the photodiode, the sensitivity of the detector is increased, thereby reducing the measurement coefficient of variance.

The photodiode's low amplitude current pulses are amplified, filtered and processed by a downstream signal processing circuit to provide a measure of radon gas concentration. The signal processing circuit includes a first stage having a DC and low frequency blocking capacitor coupled in a series circuit path from the photodiode to a bandpass amplifier circuit. The bandpass amplifier circuit amplifies only those electrical signals generated by the alpha particle-detecting photodiode that fall within a prescribed passband, which limits signals to a range up to a frequency on the order of 200 Hz, which is associated with the relatively slow rise times of output pulses produced by photodiode in response to alpha particle impingement.

The bandpass amplifier circuit has a feedback circuit comprised of a resistor and a capacitor, the values of which are chosen to control amplifier gain, so that the desired amplification of alpha particle representative signals is achieved, while high frequency noise components in excess of the bandpass cut-off are excised from the signal path at the output of bandpass amplifier circuit. For further thermal and other high frequency noise immunity, by-pass capacitors are connected between ground and the input and the output, respectively, of the bandpass amplifier.

The output of the bandpass amplifier is coupled through a further DC blocking capacitor and resistor to a threshold amplifier circuit. The threshold amplifier circuit has its output coupled to a pulse shaping circuit, such as a monostable multivibrator. The pulse shaping circuit produces square wave pulse signals for those electrical signals out of the bandpass amplifier circuit whose magnitudes exceed a predetermined threshold. This predetermined threshold is set at a value determined by the ratio of a feedback resistor and an input resistor. Since it has been found that true alpha particle representative pulses have an amplitude well above a prescribed noise level, the trigger reference of the threshold amplifier is set at a value which will successfully excise essentially all non-alpha particle based signals and provide a signal voltage level required to trigger pulse shaping circuit. The square wave pulses produced by the pulse shaping circuit are coupled to a pulse count analyzer, such as microprocessor. The pulse count analyzer is programmed to count pulses over a given measurement interval and to convert the thus determined count rate to radon concentration in terms of picocuries per liter, by multiplying the count rate by a predetermined calibration coefficient. The resulting data value is then coupled to a suitable output device, such as a printer or display.

The power supply employed in the radon detector of the present invention includes a battery pack in parallel with an A.C. power supply, with redundant filter capacitors at the output. Any interruptions in A.C. power or transients on the incoming power will not be transmitted to the instrument circuits because of the isolation and backup provided by the batteries of the battery pack. The detector is also capable of operating on batteries alone, providing a D.C. current, with no transients.

For this purpose, a diode rectifier connects the battery pack to the input of a dual power supply, while preventing a five volt output of a voltage regulator the regulator from attempting to charge up the batteries. If rechargeable batteries are used, the diode rectifier is omitted, allowing the A.C. power source to trickle charge the battery pack, while operating the instrument on A.C. power. To prevent vibration from causing the electronic components to generate unwanted pulses, a mechanically stable assembly is employed.

DETAILED DESCRIPTION

Figure 1:
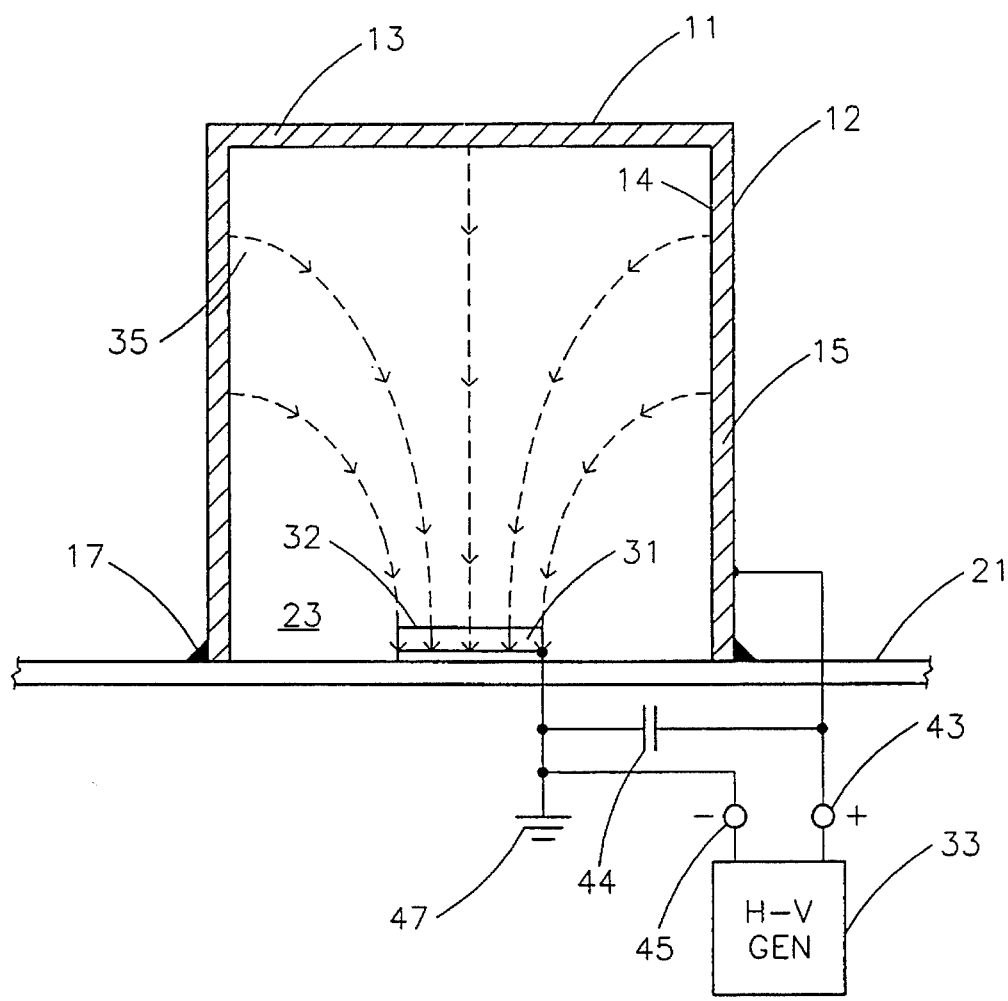
FIG. 1 diagrammatically illustrates an embodiment of the radon gas detector chamber in accordance with the present invention.

Referring now to FIG. 1, an embodiment of the radon gas detector in accordance with the present invention is diagrammatically illustrated as comprising a contaminant and light filtering enclosure 11 mounted to a circuit board 21, upon which an alpha particle-sensing photodiode 31 is mounted, whose output leads are connected to the processing electronics elsewhere on the board. As a non-limiting example, enclosure 11 may be configured in a generally cylindrical shape, and includes a top circular portion 13 and cylindrical side wall portion 15. The side wall portion 13 of the enclosure 11 adjoins top portion 15, and extends to and is joined at its base 17 in sealed engagement with circuit board 21. Photodiode 31 may comprise a commercially available photodiode, such as AG&G Vactec VTS 3080 component. The cylindrical filter enclosing the photodiode 31 also acts to shield it from electromagnetic interference (EMI).

As described previously, filter enclosure 11 is comprised of a material having a physical composition that allows radon-containing gas to pass through it, yet prevents the entry of light and radon daughter products into an interior portion (alpha particle detection chamber) 23 of the filter enclosure 11. For this purpose, the top and sides of filter enclosure 11 are preferably comprised of an electrically conductive material, such as one or more layers of porous, pressed metal, having an external surface 12 and an internal surface 14. As a non-limiting example, filter enclosure 11 may be formed of porous, pressed stainless steel having a thickness on the order one-sixteenth of an inch.

Figure 2:
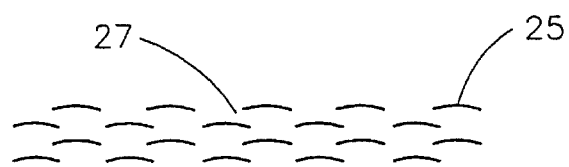
FIG. 2 diagrammatically illustrates the physical composition of a porous, pressed metallic filter as a discontinuous laminate of plural metallic layers, with discontinuities among the layers creating a radon gas diffusion path, while blocking light and radon daughter products.

As diagrammatically illustrated in FIG. 2, the physical composition of such a pressed metallic filter material generally corresponds to a discontinuous laminate or strata of plural metallic layers 25, with discontinuities 27 among the layers creating a gas diffusion path through the top 13 and side walls 15 of the filter. The generally random internal geometry of this diffusion path readily allows radon gas to pass from the exterior of the enclosure 11 to the interior alpha particle detection chamber 23. It has been found that a pressed metallic filter material having a porosity on the order of 1–40 microns is very effective in allowing radon gas to easily flow or diffuse through the filter material, without requiring a forced air flow mechanism (fan) to draw air into the interior particle detection chamber 23.

In addition, the geometry and porosity of the pressed metal filter also causes both attached and unattached Po-214 and Po-218 ions present in (radon-containing) gas passing through the filter material to be captured prior to their entering detection chamber 23. As a consequence, any such radon daughter product contaminants are prevented from corrupting the radon measurement process carried out within in detection chamber 23. Moreover, as noted briefly above, because the diffusion path through the porous metal filter is tortuous to light, it very effectively blocks the entry of electromagnetic radiation (photons) into alpha particle detection chamber 23 of the enclosure 11, so that an alpha particle detector 31 mounted within chamber 23 is not affected by the ambient light conditions of the environment in which the radon detector is placed.

In order to minimize the potential of photodiode 31 itself to be a source of background or contamination noise, during instrument manufacture, it is preferred that each photodiode be screened through background testing, so that if a photodiode undesirably exhibit excess noise, it may be rejected. Still, as will be described below with reference to FIG. 3, filtering elements are installed in the signal processing path, to remove contaminant noise.

In accordance with the invention, no voltage differential is applied across the anode and cathode electrodes of photodiode 31, so that its photosensitive PN is unbiased. As a result, photodiode 31 operates in a photovoltaic mode, which eliminates Schottky (shot) noise caused by applying a reverse bias to the PN junction. In the photovoltaic mode, photodiode 31 is operative to produce low amplitude current pulses, in response to the impingement of alpha particles thereon.

Because of the above-described physical properties of the porous metal filter 11, alpha particles which are incident upon photodiode element 31 and give rise to its generation of electrical signals (in the form of current pulses) are effectively only those alpha particles, which result from the decay of radon-containing gas that has entered the detection chamber 23. Namely, radon gas that has entered alpha particle detection chamber 23 through filter 11 decays into positively charged ionic daughter products Po-214 and Po-218. When the radon gas decays into a positively charged Po-218 ion, an alpha particle is emitted. Similarly, when the positively charged Po-218 ion further decays into Po-214, another alpha particle is emitted. Once Po-214 has emitted an alpha particle, no further alpha particle emission takes place and the resulting product is effectively biologically benign. As noted earlier, because the half lives of Po-218 and Po-214 are on the order of three minutes and less than a second, respectively, it is important that they be rapidly collected on a detection surface where alpha particle emission can be detected.

To optimize the ability of photodiode 31 to detect both of these alpha particle emissions, a high voltage 33 is applied to filter enclosure 11, which creates a static electric field, flux lines of force of which are represented by dotted lines 35, between the top and side walls of the electrically conductive filter enclosure 11 and photodiode element 31. In particular, high voltage generator 33 provides a high positive (+) voltage to conductive filter 11, relative to photodiode 31. Such a high voltage differential creates an electric field having force flux lines 35 that cause the above-mentioned Po-218 ions to be rapidly repelled away from filter enclosure 11 and accelerated toward photodiode element 31, so that they may quickly deposit upon the collection surface 32 of photodiode 31, where they decay, producing detectable alpha particles. (Approximately 88% of the Po-218 atoms produced as radon decays are singly ionized positive ions (i.e. deficient by one electron charge. Although such ions will deposit on any surface at random, with the presence of the accelerating field, they are readily focussed upon the photodiode where they neutralize their positive charge.) The ions will each experience an accelerating force in Newtons of $F=qE$, where $q=1.6\times10^{-19}$ coulombs, and E=electric field intensity in volts/meter.

As a non-limiting example, a high voltage DC power source 33 that generates a static electric field on the order of 100 volts per centimeter, may be applied between the top 13 and side walls 15 of conductive filter structure 11 and photodiode 31, such that its positive (+) terminal 43 is connected to filter 11, and its negative (−) terminal 45 connected to a housing or detector casing ground 47, to which photodiode element 31 is physically and electrically connected. Thus, the 100 V/cm field will produce a force of $1.6\times10^{-15}$ Newtons on Po-218 ions, causing such ions to be rapidly focussed onto photodiode 31. To reduce potential electromagnetic interference (EMI) coupling into the signal leads of high voltage source 33, an AC bypass impedance (capacitor) 44 is connected between positive (+) high voltage lead 43 and housing ground 47.

It should also be noted that the applied electric field 35, through which rapid collection of the decaying (alpha particle-emitting Po-218 and Po-214) daughter products is effected, also serves to minimize the opportunity of even trace amounts of water vapor molecules or other components, such as $O_2$, NO, $NO_2$, and $NH_3$, that may be present in air that has diffused into interior chamber 23, to neutralize Po-218 ions and hinder their deposition on collection surface 32. Indeed, it has been found that variations in the air humidity may produce errors in radon measurements of 30% or greater. By using an electric field to accelerate the Po-218 ions toward the photodiode 31, to reduce transit time and minimize neutralization by water vapor molecules, the accuracy of the detector is enhanced, thereby removing variability of alpha particle detection measurements due to changes in humidity.

Since an Po-218 ion emits an alpha particle as it decays into Po-214, then, with the static electric field 35 rapidly causing such daughter products of radon gas that has diffused into detection chamber 23 to deposit onto the collection surface 32 of photodiode 31, it can be expected that the emission of an alpha particle by a deposited Po-218 daughter product will occur where intended—at the collection surface 32 of the photodiode 31—so that the emitted alpha particle will be detected, thereby causing photodiode 31 to generate a small amplitude current pulse. Similarly, as the Po-214 ion (into which the deposited Po-218 has decayed) decays, it emits another alpha particle at the collection surface 32 of photodetector 31, causing generation of a further low amplitude current pulse.

Thus, since the accelerating electric field increases the number of Po-218 ions deposition upon the collection surface of photodiode 31, the sensitivity of the detector is enhanced. It has been determined that the sensitivity of an instrument detecting 0.3 alpha counts per hour for each picocurie per liter of radon can be increased by an order of magnitude or greater in accordance with the present invention. This increase in sensitivity reduces the measurement coefficient of variance (alpha particle counting error) from a value on the order of ten percent to a value of three percent for the same measurement (sampling) time.

Figure 3:
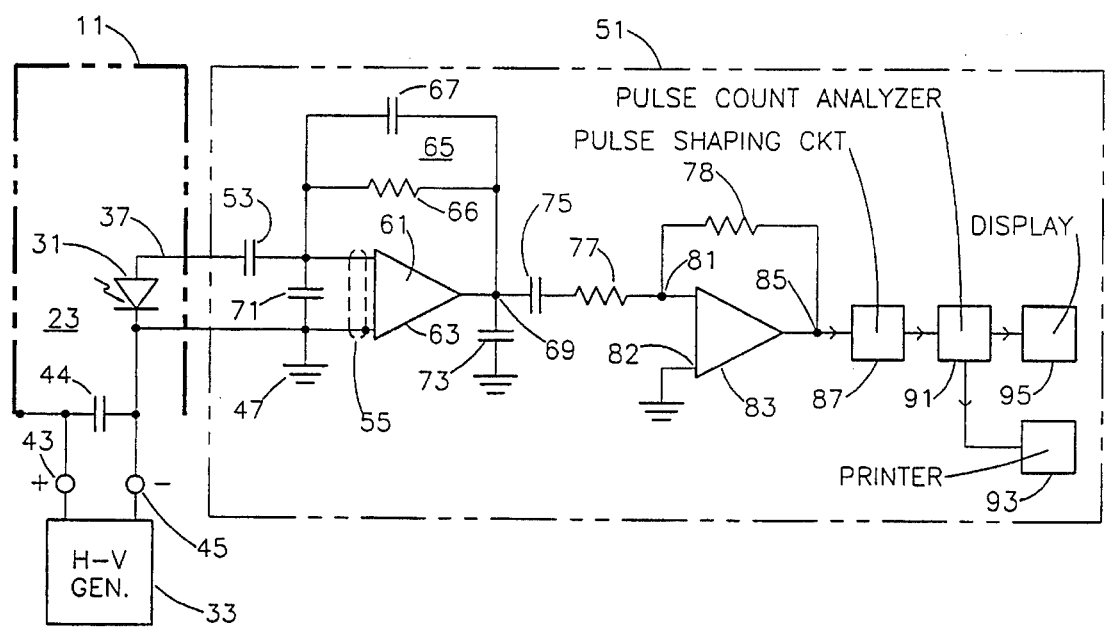
FIG. 3 schematically illustrates the signal processing flow path of the radon gas detector of the present invention.

The manner in which these low amplitude current pulses are amplified, filtered and processed to provide a measure of radon gas concentration will now be described with reference to FIG. 3, which schematically illustrates the radon gas detector of the present invention as including a signal processing circuit 51, which is coupled to process the electrical pulses generated by photo diode element 31, so as to provide an indication of the concentration of detected radon gas, based upon the number of detected alpha particle detection pulses produced by photodiode 31 over a given measurement interval.

More particularly, the front end of the signal processing circuit 51 includes a DC and low frequency blocking capacitor 53 coupled in a series circuit path from the output 37 of photodiode 31 to an inverting (−) input 61 of a bandpass amplifier circuit 63.

DC current flow is an undesirable noise that may be produced by excess noise in the form of what is commonly referred to as flicker or popcorn noise, or dark current from imperfections in the photodiode, or contaminants other than alpha particle impingement. Fortunately, present day methods of refining lead solder used in photodiode lead attachment have effectively eliminated lead solder as a source of contamination of photodiode leads. A guard trace 55 on the circuit board encircles the input to amplifier 63 to shield it from EMI.

Bandpass amplifier circuit 63 is operative to amplify only those electrical signals generated by the alpha particle detector that fall within a given frequency band, in particular a passband which limits signals to a range up to a frequency on the order of 200 Hz, and associated with the relatively slow (on the order of 1–2 ms) rise times of output pulses produced by photodiode 31 in response to alpha particle impingement.

For this purpose, bandpass amplifier circuit 63 has a feedback circuit 65 comprised of a resistor 66 and capacitor 67, values of which are chosen to control amplifier gain, so that the desired amplification of alpha particle representative signals is achieved, while high frequency (noise) components in excess of the bandpass cut-off (e.g. 200 Hz in the present example) are effectively excised from the signal path at the output of bandpass amplifier circuit 63.

In addition, for further thermal and other high frequency noise immunity, by-pass capacitors 71 and 73 are connected between ground 47 and the input 61 and the output 69, respectively, of bandpass amplifier circuit 63.

The signal path output 69 of bandpass amplifier 63 is coupled through a further DC blocking capacitor 75 and resistor 77 to a first inverting (−) input 81 of a threshold amplifier circuit 83. Threshold amplifier circuit 83 has a second, non-inverting (+) input 82 referenced to ground, and its output 85 coupled to a pulse shaping circuit 87, such as a monostable multivibrator. Pulse shaping circuit 87 is operative to produce well defined square wave pulse signals for those electrical signals in the passband amplified by bandpass amplifier circuit 63, whose magnitudes exceed a predetermined threshold. This predetermined threshold is set at a value determined by the ratio of a feedback resistor 78 and input resistor 77.

From a practical standpoint, it has been found that substantially all noise pulses will tend to have a peak-to-peak excursion on the order of 10–30 mV, while true alpha particle representative pulses have an amplitude well above this (noise) level, well up to values on the order of 150 mV. As a result, the threshold of amplifier 83 may be set at a value on the order of 50 mV or more, for example in a range on the order of from 50–80 mV, which will successfully excise essentially all non-alpha particle based signals and provide a signal voltage level required to trigger pulse shaping circuit 87.

The square wave pulses produced by pulse shaping circuit 87 are coupled to a pulse count analyzer 91, which is preferably implemented by means of a microprocessor. Pulse count analyzer 91 is programmed to count pulses over a given measurement interval and to convert the thus determined count rate to radon concentration in terms of picocuries per liter, by multiplying the count rate by a predetermined calibration coefficient. The resulting data value may then be coupled to a suitable output device, such as a printer 93 or display 95.

Figure 4:
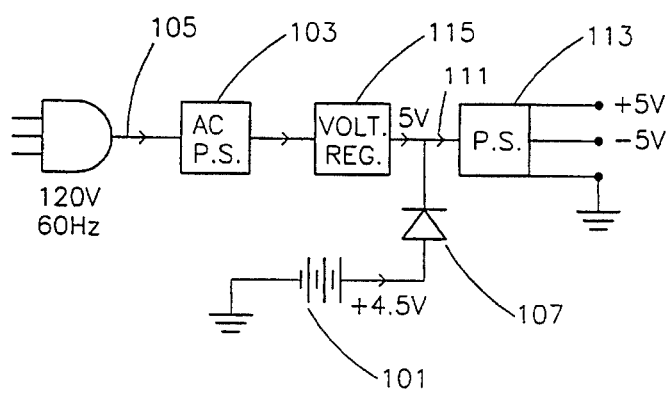
FIG. 4 shows a power supply for the radon gas detector of the present invention.

FIG. 4 diagrammatically illustrates a power supply that may be employed in the radon detector of the present invention as including a D.C. battery pack 101 in parallel with an A.C. power supply 103. Interruptions in A.C. power or transients on an incoming A.C. powerline 105 will not be transmitted to the instrument circuits because of the isolation and backup provided by the batteries of the battery pack 101. For this purpose, a diode rectifier 107 connects the battery pack 101 to an input 111 of a dual power supply unit 113, while preventing a five volt output of a voltage regulator 115 from attempting to charge up the batteries of battery pack 101. If rechargeable batteries are used, diode rectifier 107 is omitted, allowing the A.C. power source input on line 105 to trickle charge the battery pack, while operating the instrument on A.C. power. The output of dual power supply unit 113 comprises customary ±5 volt and ground potential levels, as shown.

As will be appreciated from the foregoing description, by using an electrically charged pressed, porous metal filter that allows radon gas diffusion, while blocking ambient light, the radon detector of the present invention provides a reduced hardware complexity device that readily traps both attached and unattached Po-214 and Po-218 ions, that may be present in gas passing through the filter, prior to their entering the detection chamber, so that such radon daughter products are prevented from corrupting the radon measurement process carried out within the detection chamber. Since no voltage differential is applied across its PN junction, the photodiode element operates in a photovoltaic mode, which avoids the problem of Schottky noise, producing low amplitude current pulses, which are amplified, passband filtered, and thresholded to provide well-defined pulses that are counted over a given measurement interval and converted to radon concentration in terms of picocuries per liter.

While I have shown and described an embodiment in accordance with the present invention, it is to be understood that the same is not limited thereto but is susceptible to numerous changes and modifications as known to a person skilled in the art, and I therefore do not wish to be limited to the details shown and described herein but intend to cover all such changes and modifications as are obvious to one of ordinary skill in the art.

What is claimed:

1. A device for detecting the presence of radon in a monitored gas comprising:

an electrically conductive filter enclosure comprised of an electrically conductive material that is physically configured to allow radon-containing gas to pass therethrough, while preventing the entry of light and radon daughter products into an interior portion of said electrically conductive filter enclosure;

an alpha particle detector element supported within said interior portion of said electrically conductive filter enclosure, said alpha particle detector being operative to generate electrical signals in response to the incidence thereon of alpha particles emitted from daughter products into which said radon-containing gas that has entered into said interior portion of said electrically conductive filter enclosure has decayed;

a signal processing circuit coupled to process said electrical signals generated by said alpha particle detector element and to produce an output signal representative of the presence of radon gas; and wherein said electrically conductive filter enclosure is positively charged, establishing an electric field between said electrically conductive filter enclosure and said alpha particle detector element, thereby causing radon daughter products present within said electrically conductive filter enclosure to be directed upon said alpha particle detector element.

2. A device according to claim 1, wherein said material of said electrically conductive filter enclosure is a porous, pressed metal.

3. A device according to claim 2, wherein a differential voltage is applied between said electrically conductive filter enclosure and said alpha particle detector element, such that radon daughter products present within said electrically conductive filter enclosure are repelled from said electrically conductive filter enclosure and are accelerated to impingement upon said alpha particle detector element.

4. A device according to claim 3, wherein said signal processing circuit includes a bandpass filter, that it is operative to process only those electrical signals generated by said alpha particle detector that fall within a given frequency band.

5. A device according to claim 1, wherein said alpha particle detector element includes a PN junction across which no differential voltage is applied.

6. A device according to claim 1, wherein said alpha particle detector element comprises a PN junction diode across anode and cathode electrodes of which no differential voltage is applied, so that said PN junction diode operates in photovoltaic mode, producing electrical pulse signals in response to impingement of alpha particles thereon.

7. A device according to claim 6, wherein said electrically conductive filter enclosure is applied with a voltage positive relative to said PN junction diode, such that radon daughter products present within said electrically conductive filter enclosure are repelled from said electrically conductive filter enclosure and are accelerated to impingement upon said PN junction diode.

8. A device according to claim 1, wherein said electrically conductive filter enclosure is coupled to an A.C. ground through a low impedance path of a high voltage generator through which said electrically conductive filter enclosure is positively charged, said electrically conductive filter being operative to shield said alpha particle detector element from electromagnetic interference.

9. A device according to claim 4, further including a grounded guard trace formed on a printed circuit board on which said bandpass filter is mounted, said grounded guard trace surrounding a high impedance input of said bandpass filter and reducing coupling to electromagnetic interference.

10. A device for detecting radon gas comprising:

a filter enclosure physically configured to allow radon gas to pass therethrough while preventing the entry of light and attached and unattached radon daughter products into an interior portion of said filter enclosure;

an alpha particle detector element supported within said interior portion of said filter enclosure, said alpha particle detector comprising a PN junction diode across anode and cathode electrodes of which no differential voltage is applied, so that said PN junction diode operates in a photovoltaic mode, producing electrical signals in response to impingement of alpha particles thereon; and a signal processing circuit coupled to receive said electrical signals generated by said PN junction diode and producing an output signal representative of the presence of radon gas in accordance with said electrical signals.

11. A device according to claim 10, wherein said filter enclosure comprises an electrically conductive material having a physical composition that is porous to the passage of radon gas therethrough, but prevents the entry of light and is operative to capture attached and unattached radon daughter products that may be present in radon gas passing through said porous, electrically conductive material of said filter enclosure and thereby prevent such captured radon daughter products from entering into said interior portion of said filter enclosure.

12. A device according to claim 11, wherein said electrically conductive material of said filter enclosure is applied with a voltage positive relative to said alpha particle detector element, such that radon daughter products, into which radon gas that has passed through said porous, electrically conductive material and has entered into said filter enclosure has decayed, are repelled therefrom and are directed to impinge upon said alpha particle detector element.

13. A device according to claim 10, wherein said signal processing circuit includes a bandpass filter that it is operative to process only those electrical signals generated by said alpha particle detector that fall within a given frequency band.

14. A device according to claim 13, wherein said signal processing circuit further includes a threshold circuit to which electrical signals filtered by said bandpass filter are coupled, said threshold circuit being operative to produce pulse signals for those electrical signals passed by said bandpass filter whose magnitudes exceed a predetermined threshold.

15. A device according to claim 14, wherein said signal processing circuit further includes a counter which is operative to count said pulse signals and to generate said output signal representative of the concentration of detected radon gas in dependence upon the number of pulse signals counted over a given measurement interval.

16. A device according to claim 10, wherein said daughter products include Po-214 and Po-218.

17. A device according to claim 11, wherein the electrically conductive material of said filter enclosure has a porosity on the order of 1–40 microns.

18. A device according to claim 10, wherein said signal processing circuit includes a low frequency blocking capacitor connected in a series circuit path with said PN junction diode, and an AC bypass low impedance connected between said series circuit path and a reference potential node.

19. A device according to claim 18, wherein said signal processing circuit includes a bandpass amplifier circuit coupled to said series circuit path and being operative to amplify only those electrical signals generated by said alpha particle detector that fall within a given frequency band.

20. A device according to claim 19, wherein said signal processing circuit further includes a threshold amplifier circuit to which electrical signals output by said bandpass amplifier circuit are coupled, said threshold amplifier circuit being operative to produce pulse signals for those electrical signals passed by said bandpass amplifier circuit whose magnitudes exceed a predetermined threshold.

21. A device according to claim 20, wherein said signal processing circuit further includes a counter which is operative to count said pulse signals and to generate said output signal representative of the concentration of detected radon gas in dependence upon the number of pulse signals counted over a given measurement interval.

22. A device according to claim 21, wherein said signal processing circuit includes a further low frequency blocking capacitor connected between said bandpass amplifier circuit and said threshold amplifier circuit.

23. A device according to claim 21, wherein said bandpass filter has a passband which limits the passage of signals therethrough in a frequency range in excess of 200 Hz.

24. A device according to claim 20, wherein said predetermined threshold is on the order of 50 mV or more.

25. A device according to claim 20, wherein said predetermined threshold is in a range on the order of from 50–80 mV.

26. A device according to claim 10, wherein said electrically conductive filter enclosure is coupled to an A.C. ground through a low impedance path of a high voltage generator through which said electrically conductive filter enclosure is positively charged, said electrically conductive filter being operative to shield said alpha particle detector element from electromagnetic interference.

27. A device according to claim 18, further including a grounded guard trace formed on a printed circuit board on which said bandpass amplifier circuit is mounted, said grounded guard trace surrounding a high impedance input of said bandpass amplifier circuit and reducing coupling to electromagnetic interference.

* * * * *